United States Patent
Zhou et al.

(10) Patent No.: US 10,368,777 B2
(45) Date of Patent: Aug. 6, 2019

(54) NON-CONTRAST DYNAMIC MRI MYOCARDIAL PERFUSION ANALYSIS AND VISUALIZATION

(75) Inventors: Xiangzhi Zhou, Vernon Hills, IL (US); Mitsue Miyazaki, Des Plaines, IL (US); Tsutomu Hoshino, Palm Harbor, FL (US)

(73) Assignee: TOSHIBA MEDICAL SYSTEMS CORPORATION, Otawara-Shi, Tochigi-Ken (JP)

(*) Notice: Subject to any disclaimer, the term of this patent is extended or adjusted under 35 U.S.C. 154(b) by 0 days.

(21) Appl. No.: 13/618,001

(22) Filed: Sep. 14, 2012

(65) Prior Publication Data

US 2014/0081125 A1   Mar. 20, 2014

(51) Int. Cl.
| | |
|---|---|
| A61B 5/00 | (2006.01) |
| A61B 5/026 | (2006.01) |
| A61B 5/055 | (2006.01) |
| G01R 33/56 | (2006.01) |
| G01R 33/385 | (2006.01) |
| G01R 33/483 | (2006.01) |
| G01R 33/563 | (2006.01) |

(52) U.S. Cl.
CPC ............ *A61B 5/055* (2013.01); *A61B 5/0044* (2013.01); *A61B 5/0263* (2013.01); *A61B 5/742* (2013.01); *G01R 33/385* (2013.01); *G01R 33/4833* (2013.01); *G01R 33/5608* (2013.01); *G01R 33/56366* (2013.01)

(58) Field of Classification Search
CPC .......... A61B 5/02; A61B 5/029; G01R 33/56; G01R 33/5607; G01R 33/5608; G01R 33/563; G01R 33/56308; G01R 33/5635; G01R 33/56366; G01R 33/4822; G06T 5/50
USPC .......................................................... 600/419
See application file for complete search history.

(56) References Cited

U.S. PATENT DOCUMENTS

| | | | |
|---|---|---|---|
| 5,377,681 A | | 1/1995 | Drane |
| 5,647,360 A | * | 7/1997 | Bani-Hashemi et al. ..... 600/425 |
| 5,722,405 A | * | 3/1998 | Goldberg ............. A61B 5/0275 |
| | | | 600/407 |

(Continued)

FOREIGN PATENT DOCUMENTS

| | | |
|---|---|---|
| CN | 102018511 A | 4/2011 |
| JP | 2005-510322 | 4/2005 |

(Continued)

OTHER PUBLICATIONS

Peled et al. "High b-value Apparent Diffusion-Weighted Images from Curve-ball DTI." J Magn Reson Imaging. Jul. 2009; 30(1): 243-248.*

(Continued)

*Primary Examiner* — Amelie R Gillman
(74) *Attorney, Agent, or Firm* — Nixon & Vanderhye P.C.

(57) ABSTRACT

Black blood time to inversion (BBTI) tag-on and tag-off images acquired by magnetic resonance imaging (MRI) are analyzed to produce difference magnitude 3D images as a function of time (BBTI values) representing blood perfusion in a region of interest (ROI). Perfusion data of the ROI having values which are different for normal and abnormal myocardial tissues are displayed for plural slices of a 3D image and for plural BBTI values in a single display panel.

26 Claims, 13 Drawing Sheets

(56) References Cited

U.S. PATENT DOCUMENTS

| | | | |
|---|---|---|---|
| 5,827,187 A * | 10/1998 | Wang et al. | 600/419 |
| 5,908,386 A * | 6/1999 | Ugurbil et al. | 600/410 |
| 6,564,080 B1 * | 5/2003 | Kimura | 600/410 |
| 8,725,235 B2 * | 5/2014 | Gielen | A61B 5/06 382/128 |
| 2002/0151780 A1 * | 10/2002 | Klotz | 600/407 |
| 2004/0082846 A1 * | 4/2004 | Johnson | A61B 5/02014 600/410 |
| 2006/0056692 A1 * | 3/2006 | Assmann | 382/173 |
| 2006/0241412 A1 | 10/2006 | Rinck et al. | |
| 2007/0203412 A1 | 8/2007 | Sugiura | |
| 2008/0009729 A1 * | 1/2008 | Esham | A61B 8/08 600/438 |
| 2008/0064947 A1 * | 3/2008 | Heruth | A61B 19/52 600/407 |
| 2009/0005672 A1 | 1/2009 | Sugiura | |
| 2009/0148020 A1 * | 6/2009 | Sugiura | A61B 5/055 382/131 |
| 2009/0220050 A1 | 9/2009 | Guhring et al. | |
| 2011/0071382 A1 | 3/2011 | Miyazaki et al. | |
| 2011/0080170 A1 * | 4/2011 | Miyazaki | 324/309 |
| 2011/0249005 A1 | 10/2011 | Hautvast | |
| 2012/0078085 A1 | 3/2012 | Xue et al. | |
| 2012/0082352 A1 | 4/2012 | Hundley et al. | |
| 2012/0189183 A1 * | 7/2012 | Xue | G06T 7/0024 382/131 |
| 2013/0116545 A1 * | 5/2013 | Xu | A61B 5/0044 600/413 |

FOREIGN PATENT DOCUMENTS

| | | |
|---|---|---|
| JP | 2005-137558 | 6/2005 |
| JP | 2005-137558 A | 6/2005 |
| JP | 2006-087626 | 4/2006 |
| JP | 2009-535139 | 10/2009 |
| JP | 2011-083592 | 4/2011 |
| JP | 2012-105982 | 6/2012 |
| WO | WO 2005/044104 A1 | 5/2005 |

OTHER PUBLICATIONS

International Search Report dated Oct. 29, 2013, 2013 in PCT/JP2013/075056.

Kim, et al., "Relationship of MRI Delayed Contrast Enhancement to Irreversible Injury, Infarct Age, and Contractile Function," Circulation Journal of the American Heart Association, pp. 1991-2002 (Nov. 9, 1999).

Nandalur, et al., "Diagnostic Performance of Stress Cardiac Magnetic Resonance Imaging in the Detection of Coronary Artery Disease," Journal of the American College of Cardiology: Cardiac Imaging, vol. 50, No. 14, pp. 1343-1353 (Oct. 2, 2007).

Dall' Armellina, et al., "CMR for characterization of the myocardium in acute coronary syndromes," Nature Reviews, Cardiology, vol. 7, pp. 624-636 (Nov. 2010).

Cerqueira, et al., "Standardized Myocardial Segmentation and Nomenclature for Tomographic Imaging of the Heart: A Statement for Healthcare Professionals From the Cardiac Imaging Committee of the Council on Clinical Cardiology of the American Heart Association," vol. 105, pp. 539-542 (2002).

Ortiz-Perez, et al., "Correspondence Between the 17-Segment Model and Coronary Arterial Anatomy Using Contrast-Enhanced Cardiac Magnetic Resonance Imaging," Journal of the American College of Cardiology: Cardiovascular Imaging, vol. 1, No. 3, pp. 282-293 (May 2008).

Extended European Search Report dated Mar. 17, 2016 in EP 13837210.7.

Office Action dated Sep. 23, 2016 in CN 201380043226.3.

* cited by examiner

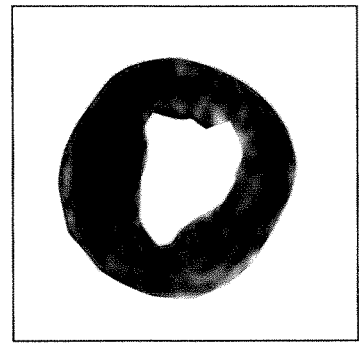
Fig. 5B After Registration
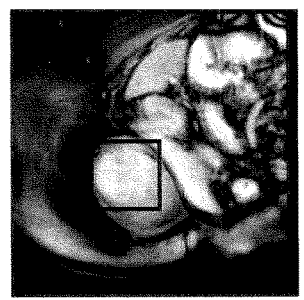
Fig. 5A Before Registration
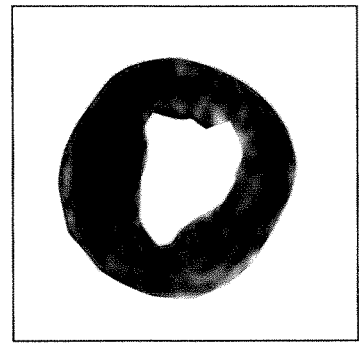
Fig. 6C Non-myocardial signal removed
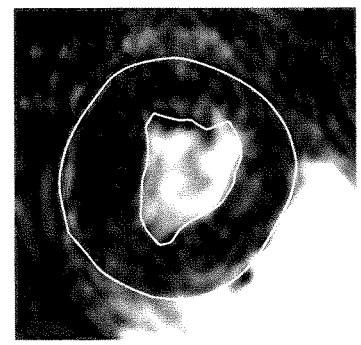
Fig. 6B Apply the ROI on the subtracted images
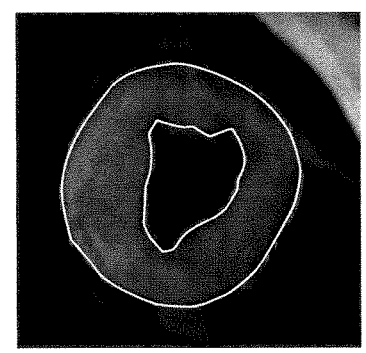
Fig. 6A Segmentation on Tag-on or Tag-off images

NON-CONTRAST DYNAMIC MRI MYOCARDIAL PERFUSION ANALYSIS AND VISUALIZATION

RELATED APPLICATION

This application is related to our copending application Ser. No. 13/587,294 filed Aug. 16, 2012, which is hereby incorporated by reference.

FIELD

The subject matter described below relates generally to magnetic resonance imaging (MRI) apparatus and process. In particular, the MRI apparatus and method described below provide non-contrast dynamic MRI myocardial perfusion analysis and visualization.

BRIEF DESCRIPTION OF THE DRAWINGS

FIGS. 5A and 5B illustrate left ventricle (LV) magnitude images (e.g., resulting from the process of FIG. 4) at different BBTI periods both before registration and after registration;

FIGS. 6A, 6B and 6C illustrate segmentation imposed on tag-on or tag-off images with the segmented region of interest (ROI) being superimposed on the subtracted images and a clear image where non-myocardial signals outside the segmented volume have been removed;

DETAILED DESCRIPTION OF EXEMPLARY EMBODIMENTS

Figure 1:
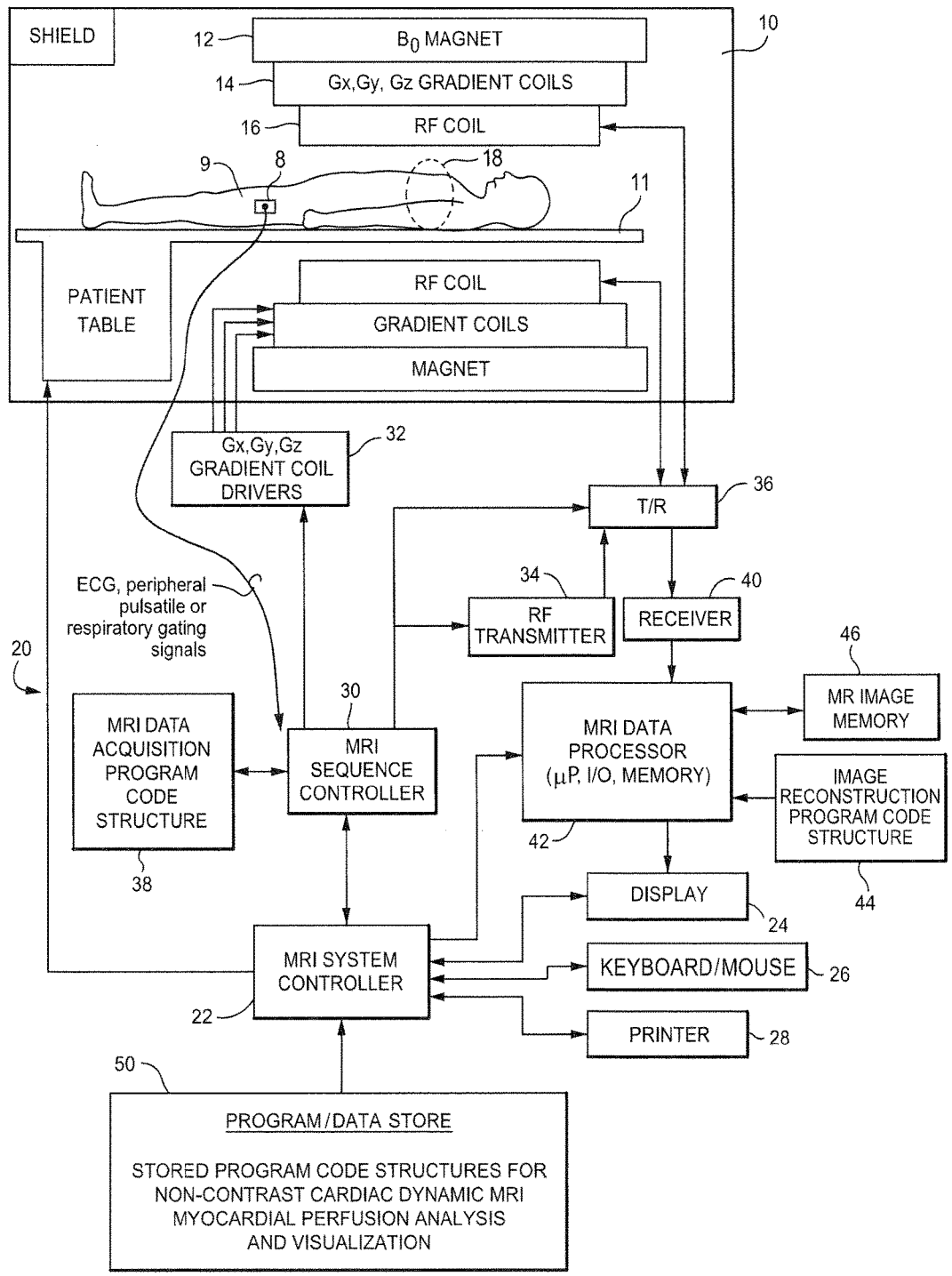
FIG. 1 is a high-level schematic block diagram of an exemplary MRI system configured to provide non-contrast dynamic MRI myocardial perfusion analysis and visualization.

The MRI system shown in FIG. 1 includes a gantry 10 (shown in schematic cross-section) and various related system components 20 interfaced therewith. At least the gantry 10 is typically located in a shielded room. The MRI system geometry depicted in FIG. 1 includes a substantially coaxial cylindrical arrangement of the static field Bo magnet 12, a Gx, Gy and Gz gradient coil set 14 and an RF coil assembly 16. Along the horizontal axis of this cylindrical array of elements is an imaging region 18 shown as substantially encompassing the anatomy of interest (i.e., region of interest or "ROI") for a patient 9 (e.g., the heart for cardiac MRI) supported by a patient bed or table 11.

An MRI system controller 22 has input/output ports connected to display 24, keyboard/mouse 26 and printer 28. As will be appreciated, the display 24 may be of the touch-screen variety so that it provides control inputs as well.

The MRI system controller 22 interfaces with MRI sequence controller 30 which, in turn, controls the Gx, Gy and Gz gradient coil drivers 32, as well as RF transmitter 34 and transmit/receive switch 36 (if the same RF coil is used for both transmission and reception). As those skilled in the art will appreciate, many different types of RF coils (e.g., whole body coils, surface coils, birdcage coils, coil arrays, etc.) may be employed to transmit and/or receive RF signals to/from the ROI in the imaging volume. As will also be appreciated, one or more suitable physiological transducers 8 may be affixed to the patient's body to provide ECG (electrocardiogram), respiratory and/or peripheral pulsatile gating signals to the MRI sequence controller 30. The MRI sequence controller 30 also has access to suitable program code structure 38 for implementing MRI data acquisition sequences already available in the repertoire of the MRI sequence controller 30—e.g., to generate non-contrast cardiac MRI tissue images using operator and/or system inputs defining particular MRI data acquisition sequence parameters, one or more ROI, etc.

The MRI system 20 includes an RF receiver 40 providing input to data processor 42 so as to create processed image data which may be sent to display 24. The MRI data processor 42 is also configured for access to image reconstruction program code structure 44 and to MR (magnetic resonance) image memory 46 (e.g., for storing MR image data derived from processing in accordance with the exemplary embodiments and the image reconstruction program code structure 44).

Also illustrated in FIG. 1 is a generalized depiction of an MRI system program/data store 50 where stored program code structures (e.g., for non-contrast cardiac MRI dynamic myocardial perfusion analysis and visualization), as well as a related graphical user interface (GUI), operator inputs to same, etc., which are stored in computer readable storage media accessible to the various data processing components of the MRI system. As those in the art will appreciate, the program store 50 may be segmented and directly connected, at least in part, to different ones of the system 20 processing computers having most immediate need for such stored program code structures in their normal operation (i.e., rather than being commonly stored and connected directly to the MRI system controller 22).

Indeed, as those skilled in the art will appreciate, the FIG. 1 depiction is a very high-level simplified diagram of a typical MRI system with some modifications so as to practice exemplary embodiments to be described hereinbelow. The system components can be divided into different logical collections of "boxes" and typically comprise numerous digital signal processors (DSP), microprocessors, special purpose processing circuits (e.g., for fast A/D conversions, fast Fourier transforming, array processing, etc.). Each of those processors is typically a clocked "state machine" wherein the physical data processing circuits progress from one physical state to another upon the occurrence of each clock cycle (or predetermined number of clock cycles).

Not only does the physical state of processing circuits (e.g., CPUs, registers, buffers, arithmetic units, etc.) progressively change from one clock cycle to another during the course of operation, the physical state of associated data storage media (e.g., bit storage sites in magnetic storage media) is transformed from one state to another during operation of such a system. For example, at the conclusion of an MR imaging reconstruction process, an array of computer-readable accessible data value storage sites (e.g., multi-digit binary representations of pixel values) in physical storage media will be transformed from some prior state (e.g., all uniform "zero" values or all "one" values) to a new state wherein the physical states at the physical sites of such an array (e.g., of pixel values) vary between minimum and maximum values to represent real world physical events and conditions (e.g., the tissues of a patient over an imaged region space). As those in the art will appreciate, such arrays of stored data values represent and also constitute a physical structure—as does a particular structure of computer control program codes that, when sequentially loaded into instruction registers and executed by one or more CPUs of the MRI system 20, cause a particular sequence of operational states to occur and be transitioned through within the MRI system.

The exemplary embodiments described below provide improved ways to acquire and/or process MRI data acquisitions and/or to generate and display MR images.

Use of an injected gadolinium (Gd)-based contrast agent (possibly in association with an injected stress perfusion agent) is known, but use of such contrast agents is often not an acceptable MRI technique for detecting infarct and ischemic lesions in myocardium. Late gadolinium contrast enhancement (LGE) is based on measuring a difference between normal and infarct myocardium by observing MRI T1-contrast (wash-out) of the gadolinium contrast agent via observed MRI signals from the myocardium after injection. In order to obtain a realistic observation of myocardium under stress, such stress may be induced by patient physical exercise or injected drug-induced stress (intended to cause increase in heart rate, dilation of cardiovascular blood vessels, etc., similar to that caused by physical exercise) so as to hopefully better observe blood flow abnormalities under such transient stress situations.

Arterial Spin Labeling (ASL) has also been used for non-contrast myocardial ischemia evaluation, but this technique has been limited to a single slice at a single time point without the capability to generate perfusion curves or three-dimensional (3D) coverage. The corresponding analysis method is considerably different from our new non-contrast dynamic MRI perfusion analysis and visualization.

In particular, we have now discovered a way to avoid use of such contrast agents by achieving a non-contrast (i.e., without injection of a chemical contrast agent) MRI technique for producing myocardium perfusion curves/table data that can be used to distinguish between normal myocardium, ischemic myocardium and infarct myocardium. Indeed, even revascularized infarct myocardium (treated with revascularized techniques such as stent insertions into blood vessels, surgical bypass blood vessel operations, etc.) may be distinguished. In accordance with exemplary embodiments, such myocardium distinctions can be made within any desired region of interest (e.g., an operator-defined arbitrary region of interest, a standard American Heart Association (AHA) segment, a single pixel, etc.).

Although injection of a contrast agent (e.g., gadolinium-based) is avoided, it may still be desirable to use exemplary embodiments in combination with patient stress (either exercise-induced or drug-induced) so as to better detect abnormalities that may exist or be more prominent only during such stressed situations.

In exemplary embodiments, a set of "tag-on" (2D or 3D) MRI k-space data is acquired after an incoming volume of blood has been "tagged" with an initial spatially selective RF pulse (e.g., typically a spatially selective 180° inversion pulse) where the data acquisition subsequence starts after a given time to inversion (TI) delay time. A similar set of "tag-off" MRI data is also acquired using the same TI delay interval—but without the initial spatially selective RF tagging pulse. This technique is sometimes known in the art as black blood time to inversion (BBTI) imaging. A sequence of such tag-on/tag-off data sets for each of plural TI times is acquired in k-space.

For each given TI time, 2D/3D Fourier Transform reconstructed spatial domain tag-on and tag-off image data sets (i.e., the result of well known 2DFT/3DFT reconstruction processes) are subtracted (e.g., on a pixel-by-pixel basis) to provide BBTI blood perfusion images where blood perfusion (MR signal strength) as a function of time can be plotted or tabulated. For any given region of interest (e.g., an AHA segment, arbitrary operator-defined ROI or even a single pixel), a plot of the time sequence of data values provides a blood perfusion curve as a function of time which provides several dimensions of differentiation between perfusion curves for "normal" myocardium, abnormal ischemic myocardium, infarct myocardium—and even revascularized (treated) ischemic myocardium. As will be expected, infarct myocardium shows no perfusion (i.e., no peak or increase in detected MRI signal strength). However, ischemic myocardium has a time-delayed peak flow time of occurrence, as well as less detected signal intensity, when compared to normal (or revascularized) myocardium. Accordingly, ischemic areas can be distinguished based upon time and/or amplitude (or even integrated area under the curve) comparisons and/or comparisons to predetermined thresholds, etc.

A perfusion curve and/or a corresponding data table pertaining to a region of interest (e.g., a predetermined AHA myocardium segment or an arbitrary operator-indicated ROI or even a single pixel) that includes distinguishing characteristics so that the MRI results (e.g., as displayed to an operator or stored data for later display to others) can differently depict the ROI as representing normal, ischemic, infarct or even revascularized myocardium—all without use of any injected contrast agent (e.g., gadolinium).

Figure 2:
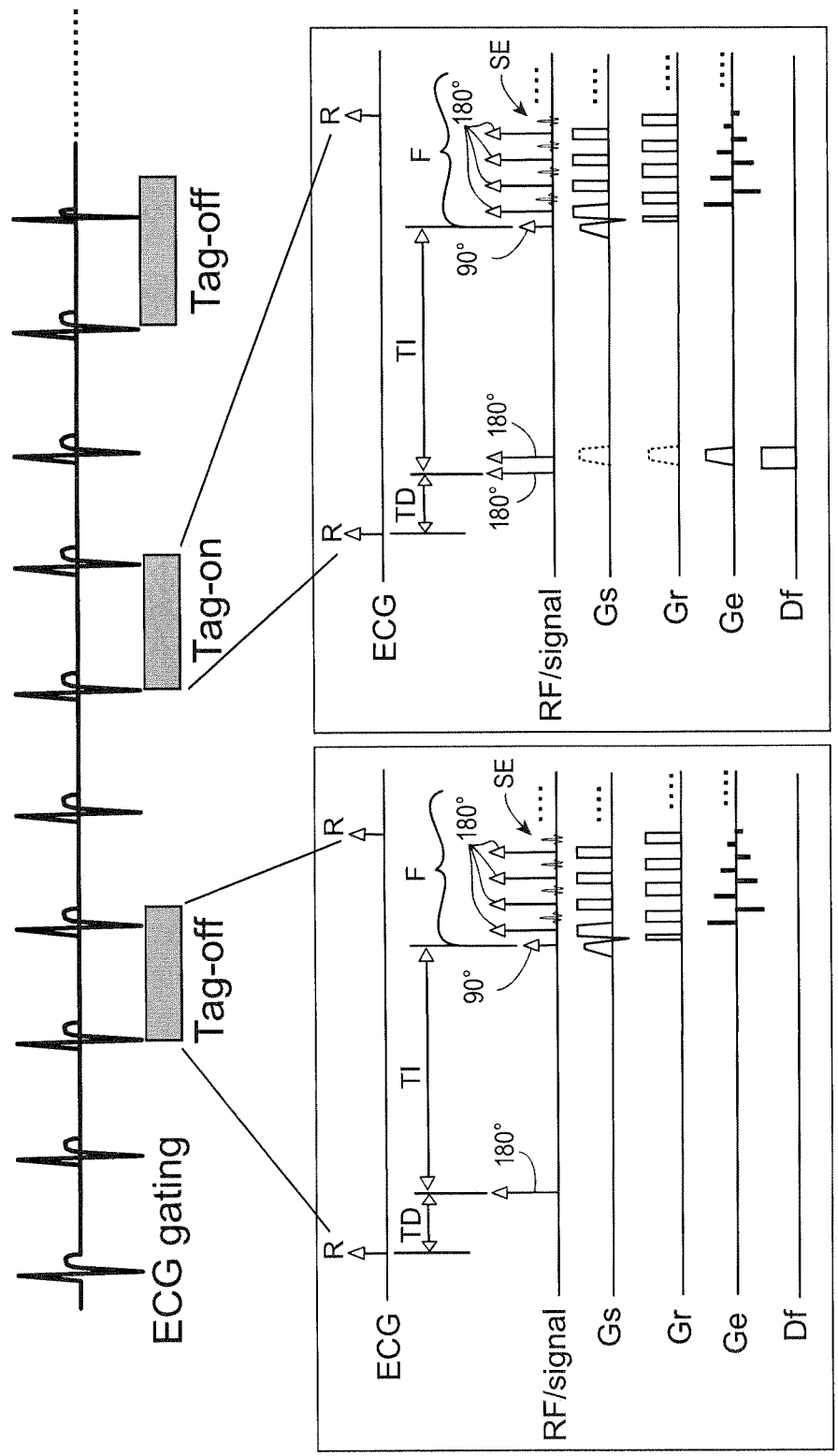
FIG. 2 is a schematic depiction of a first exemplary tag-on, tag-off MRI data acquisition sequence for use in the system of FIG. 1.

In an exemplary data acquisition sequence depicted at FIG. 2, electrocardiogram (ECG) gating is used so as to synchronize both "tag-off" and "tag-on" subsequences as depicted. In the tag-off subsequence shown to the left-lower side of FIG. 2, a short initial fixed time delay TD is employed to ensure that that the data acquisition subsequence begins its active phase during a desired diastole portion of the RST ECG signal. After delay TD, a non-selective 180° nuclear magnetic resonance (NMR) RF nutation pulse is employed (to help suppress background signals from a subsequent difference image because the signal from myocardium is relatively small, e.g., about 10% of the total MRI signal). The active phase of the actual data acquisition subsequence may, if desired, begin with a preparation pulse (e.g., a fat suppression pulse), followed by a desired data acquisition subsequence F initiated with a slice-selective (e.g., α°—typically 45° or 90°) NMR nutation pulse to initiate a desired MRI data acquisition subsequence F, e.g., a sequence of slice-selective 180° RF nutation refocusing pulses to elicit intervening RF spin echo (SE) responses during readout gradient Gr pulses, each spin echo being preceded by a phase encoding Ge magnetic gradient pulse (which is varied for different echoes so as to elicit date for a respectively corresponding line in k-space). As those in the art will appreciate, such known MRI data acquisition subsequences might be, e.g., of the balanced steady-state free precession (bSSFP) type (presently preferred) or of the fast spin echo (FSE) type or possibly of other types.

The tag-on data acquisition subsequence depicted at the right-lower side of FIG. 2 is similar to the tag-off subsequence—except that, after delay TD, there is also a spatially selective "tagging" 180° RF nutation pulse (e.g., perhaps at an oblique angle as represented by the dotted concurrent gradient pulses and the Df frequency offset pulse as depicted). As those in the art will appreciate, this will, in effect, revert a predetermined inflowing volume of blood back to a non-inverted magnetization orientation—thus "tagging" this inflowing volume of blood so that it will generate different MR signal responses than for the tag-off subsequence as the RF tagged flowing blood MR nuclei enter into the downstream ROI.

Figure 3:
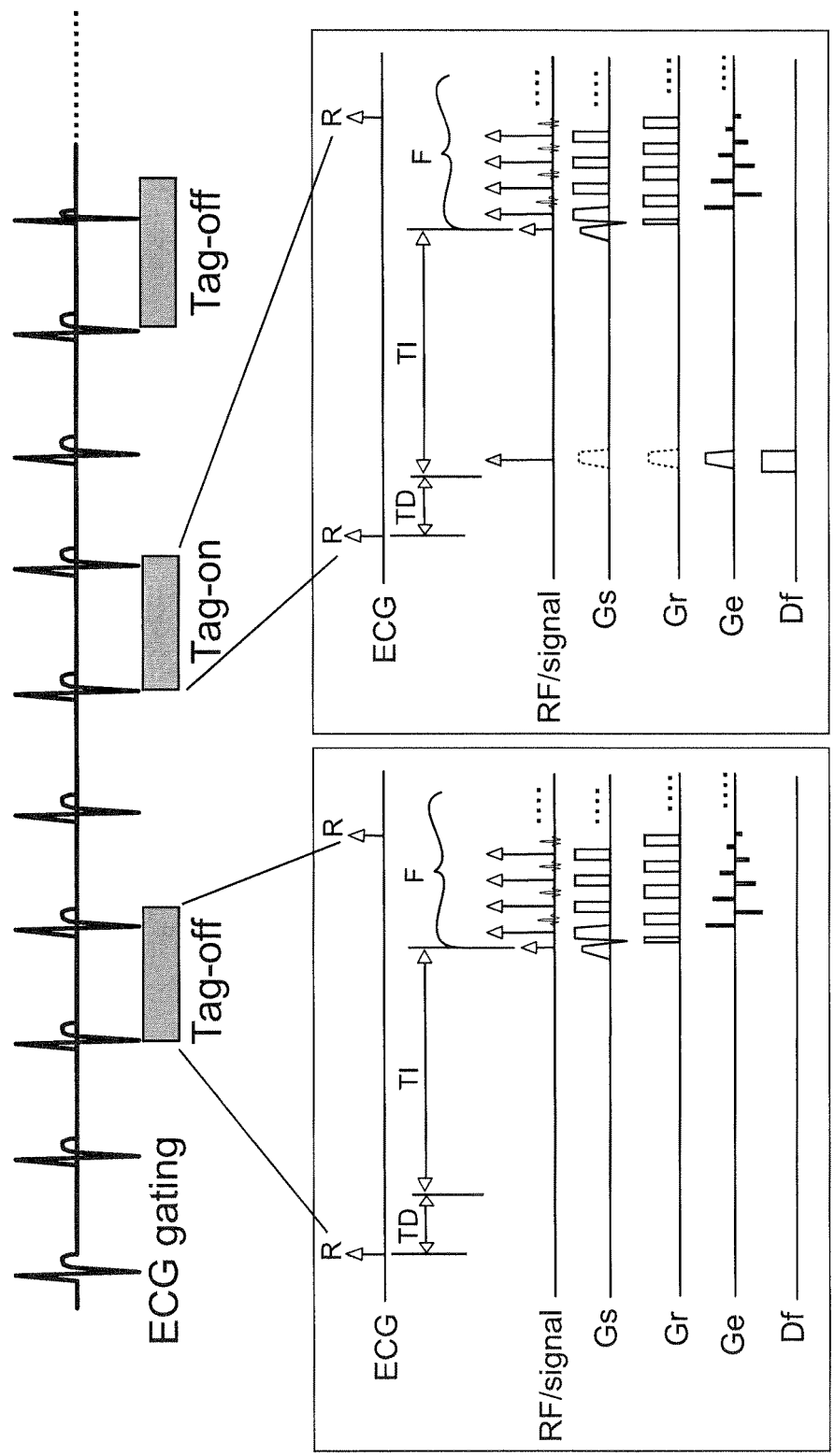
FIG. 3 is a schematic depiction of a second exemplary tag-on, tag-off MRI data acquisition sequence for use in the system of FIG. 1.

The tag-on/tag-off alternate acquisition subsequences depicted in FIG. 3 are the same as those depicted in FIG. 2, except that, as will be observed, there is no initial non-selective 180° nutation pulse (in either tag-on or tag-off subsequences) for background suppression purposes.

As depicted in dotted lines in both FIGS. 2 and 3, to achieve a desired oblique orientation for the spatially selective 180° tag-on nutation pulse, there may be concurrent usage of differently chosen magnitude Gs, Gr and Ge magnetic gradient pulses.

We now propose exemplary analysis methods that can be perhaps best suited for use with our non-contrast dynamic myocardial perfusion techniques. For example, the new methods can process a dynamic, 3D image data set with the capability to visualize blood perfusion in the left ventricle (LV) and to show perfusion curves for any segments or ROI defined by the user.

As will be understood by those in the art, our perfusion analysis and visualization methods can be incorporated into the MRI system of FIG. 1 or, alternatively, may be practiced as part of a separate image analysis/display system remotely located from the MRI system of FIG. 1 where original tag-on and tag-off image data are acquired.

For dynamic 3D images obtained from our non-contrast perfusion techniques, we propose the following exemplary presently preferred analysis procedures (not all of which may always be required or desired):

1. Perform complex data subtraction between tag-on and tag-off images.
2. Perform image registration: rigid or non-rigid registration for 3D images at different BBTI.
3. Create a histogram of tag-on and tag-off images to check for myocardium signal loss caused by suscepti-bility and/or by tagging slice affecting the imaged slice. By subtraction of histograms, adverse susceptibility and tagging slice effects on the imaged myocardium can be detected.
4. Use of myocardial segmentation.
5. Display of the segmented myocardium in a color map format.
6. Create a perfusion curve for each segment or ROI across all slices.
7. Concurrent display of all 3D slices versus BBTI.
8. Concurrent automatic display of respectively corresponding perfusion curves when selecting a segment and/or ROI.
9. Perfusion curve fitting for quantification purposes.

Figure 4:
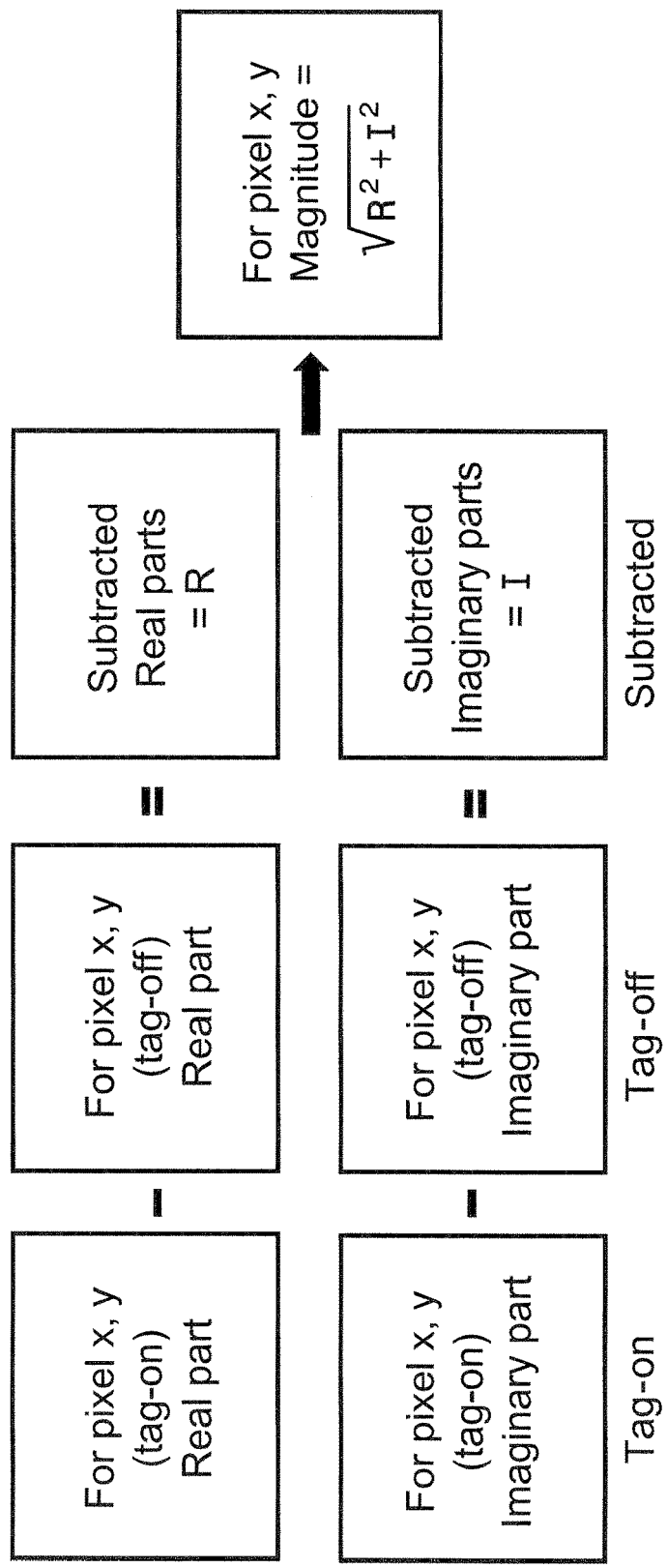
FIG. 4 illustrates subtraction of previously acquired tag-on and tag-off images on a pixel-by-pixel basis using complex-valued arithmetic so as to produce a magnitude image of the subtracted tag-on and tag-off images.

Complex data subtraction of the tag-on and tag-off image data is depicted in FIG. 4. The subtracted image should be in complex format (real and imaginary parts, R+jI) because the magnitude of subtracted pixels is then made insensitive to signal changes caused by possible phase shifts between tag-on and tag-off signals. Thus, the original tag-on and tag-off images should also be in complex-valued format. The complex-valued data after subtraction is then used to build a difference magnitude image formed by difference magnitude image data for perfusion analysis.

Since the 3D images at different BBTI are acquired at different acquisition times, registration between different BBTI images may be necessary. The example images in FIGS. 5A and 5B demonstrate the 3D registration for an imaging slab across all BBTIs (for simplicity in explanation, only one slice is shown).

Registration is not limited to rigid registration. For example, the donut shape of a left ventricle cross-section at one BBTI may have a slightly different shape at another BBTI. In this case, non-rigid registration should be performed.

Since it is desired to register the left ventricle (LV), in the proposed exemplary method, a regional registration for the LV can be performed if the registration window is placed on the LV only. If a non-selective pulse is used, the contrast between a heart chamber and the surrounding myocardium will be inverted at some BBTIs. In this case, both tag-on and tag-off images should be utilized in the registration process. For example, one can select the images with positive contrast (myocardial signal intensity SI>LV chamber blood SI) and perform registration on those. Then one can select negative contrast images and perform another registration process. The registration shift of pixels of each image relative to the reference images can be recorded for a combined registration process. Manual shifting with a visual check may be necessary to achieve the best registration.

LV segmentation can be achieved after registration by aligning the LV along successive BBTI images as depicted in FIGS. 6A, 6B and 6C. On the tag-off images, the endocardial and epicardial contours may be drawn (manually or semi-automatically) for each slice and saved. Then the saved contours can be applied onto the subtracted images. To visualize LV myocardium only, other signals can be removed (e.g., see the clear" image of FIG. 6C). Note that the LV contours should be carefully placed to exclude any contamination from artifacts (e.g., susceptibility artifacts) and tagging slice interference.

Figure 7A:
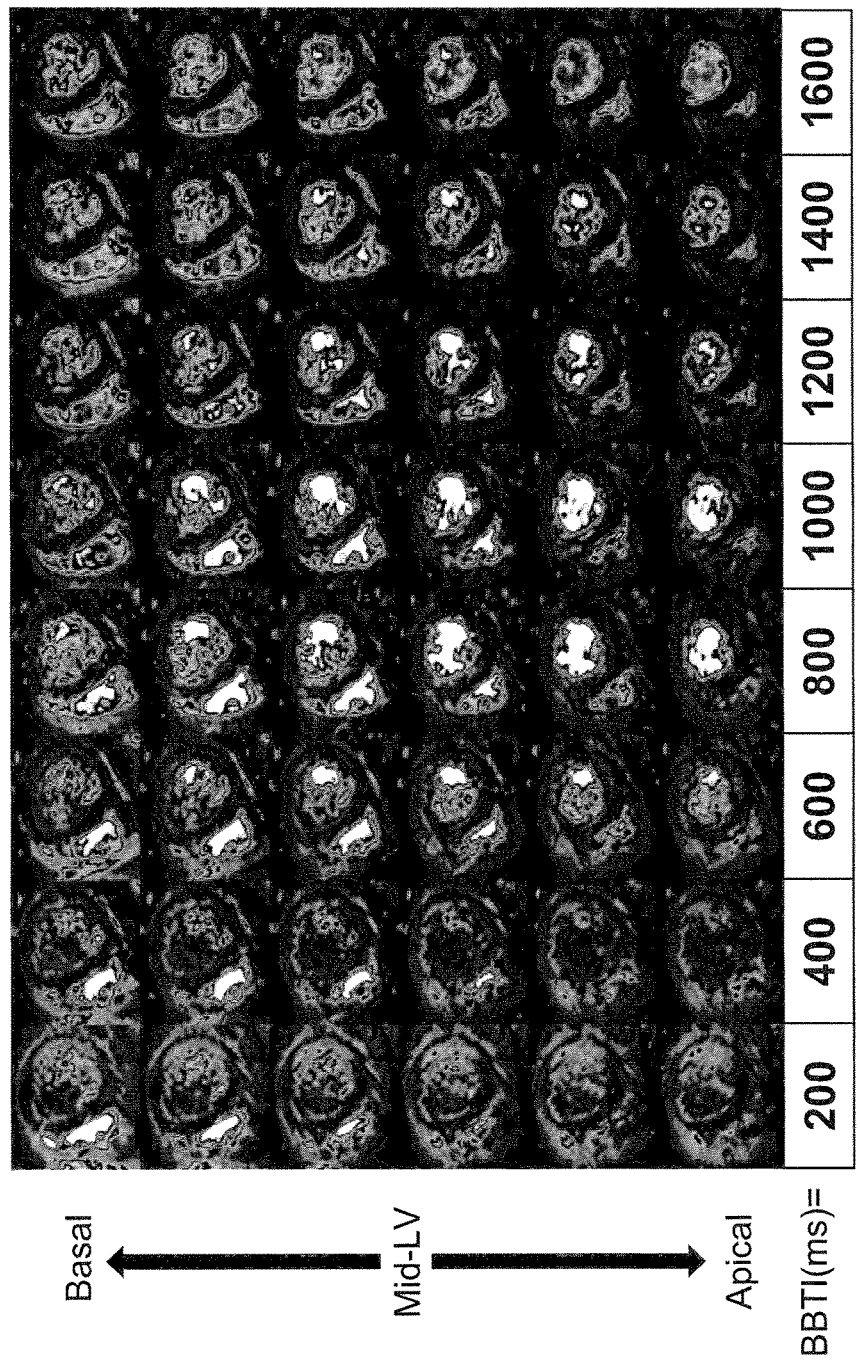
FIGS. 7A and 7B depict exemplary perfusion visualizations wherein left ventricle cross-sectional images at plural BBTI values are displayed together in one panel as a function of BBTI time periods—before LV segmentation in FIG. 7A and after segmentation in FIG. 7B.
Figure 7B:
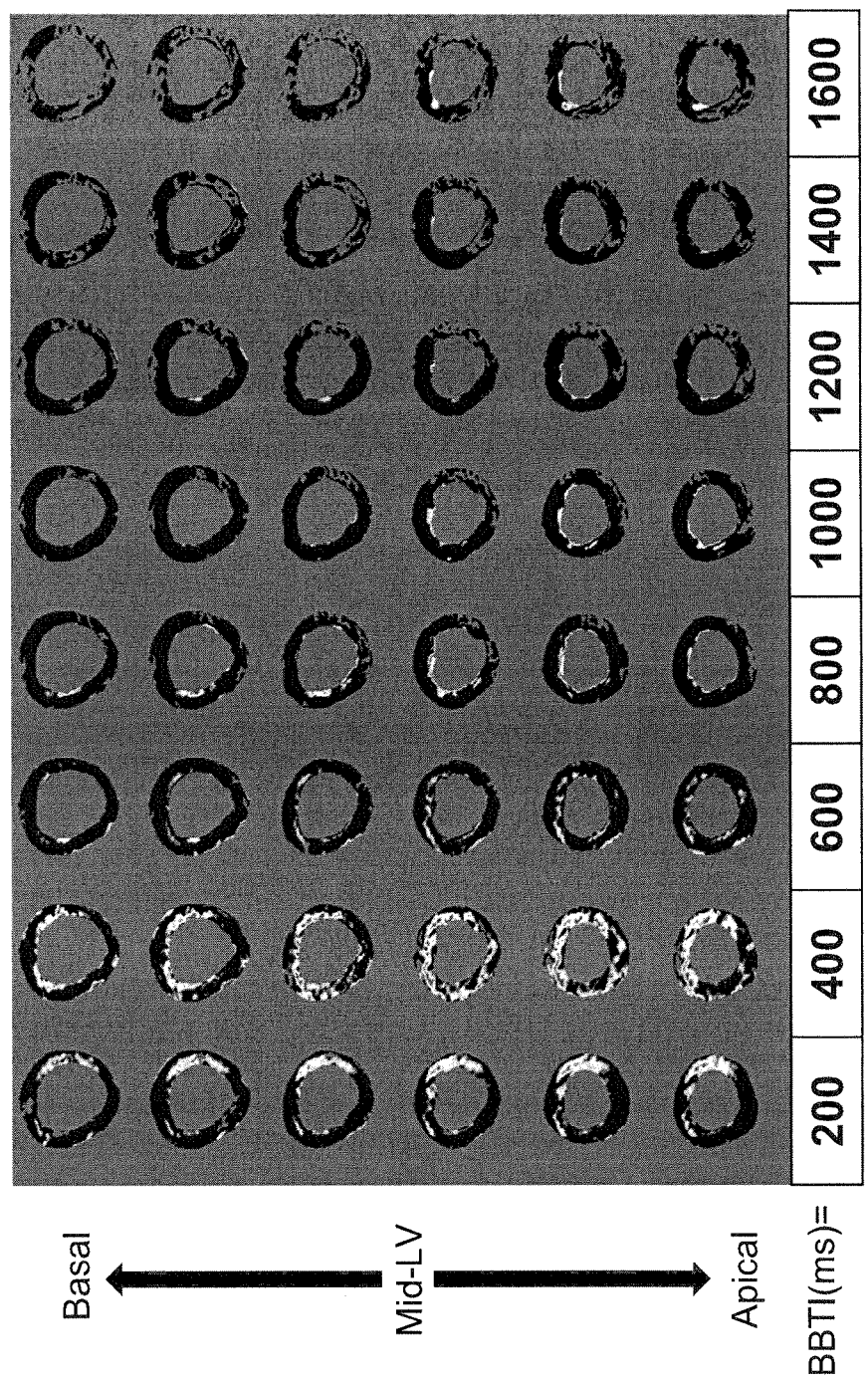
Figures 8A, 8B, 8C, 8D:
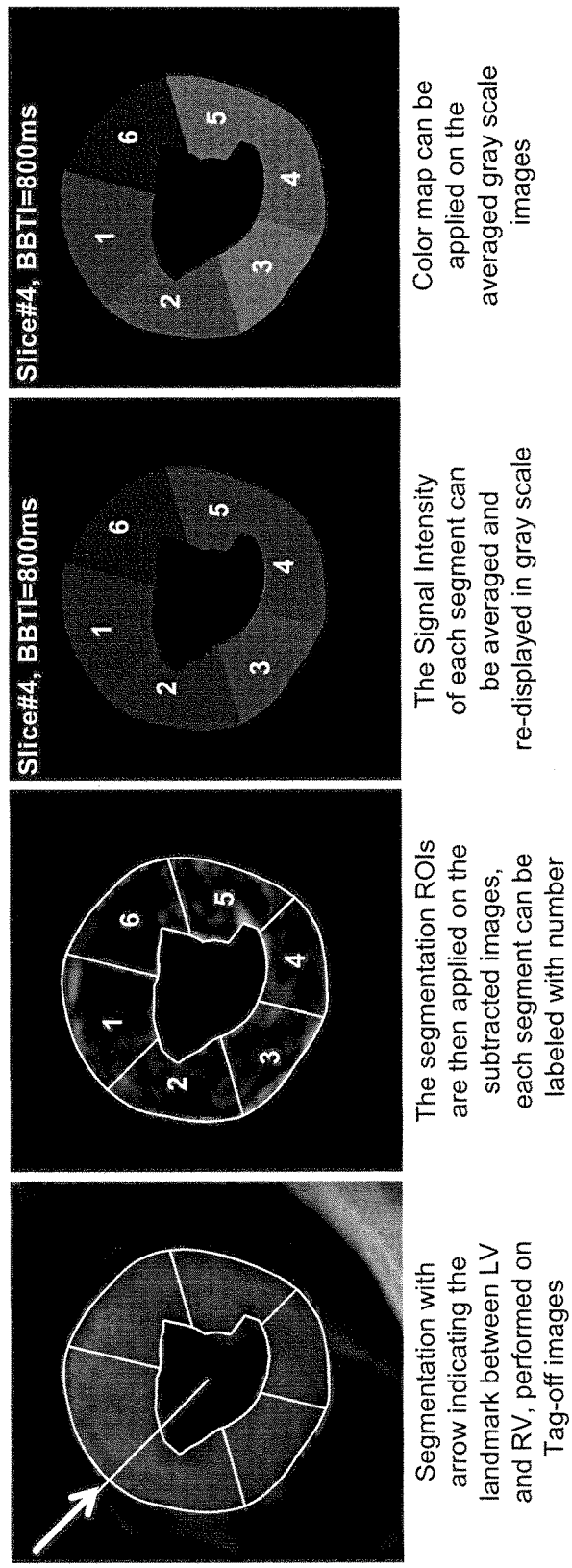
FIGS. 8A, 8B, 8C and 8D further depict an exemplary coronary artery territory segmentation in the left ventricle, here using an American Heart Association (AHA) six-segment model resulting in a color-mapped display of the segmented coronary artery territory of the left ventricle.

Perfusion visualization can be achieved as shown in FIGS. 7A-B. Here, LV images from apical to basal slices at all BBTIs are displayed in one panel. In this panel, the blood perfusion in the left ventricle can be observed (a colorized map is preferably applied to better visualize the signal intensity change). FIG. 7A depicts visualization before LV segmentation while FIG. 7B depicts visualization after segmentation.

Coronary artery territory segmentation in LV may, for example, be either the standard American Heart Association (AHA) six-segment model or, if desired, any number of other user-defined segmentation. The AHA six segmentation depicted in FIGS. 8A, 8B, 8C and 8D starts from the groove between LV and RV (right ventricle) and automatically runs clockwise. That is, the groove is marked as the start point to identify the coronary artery territory. Each succeeding numbered AHA segment can be labelled, averaged and color-mapped to distinguish and show intensity changes among all segments as depicted in FIGS. 8A-8D.

Figure 9A:
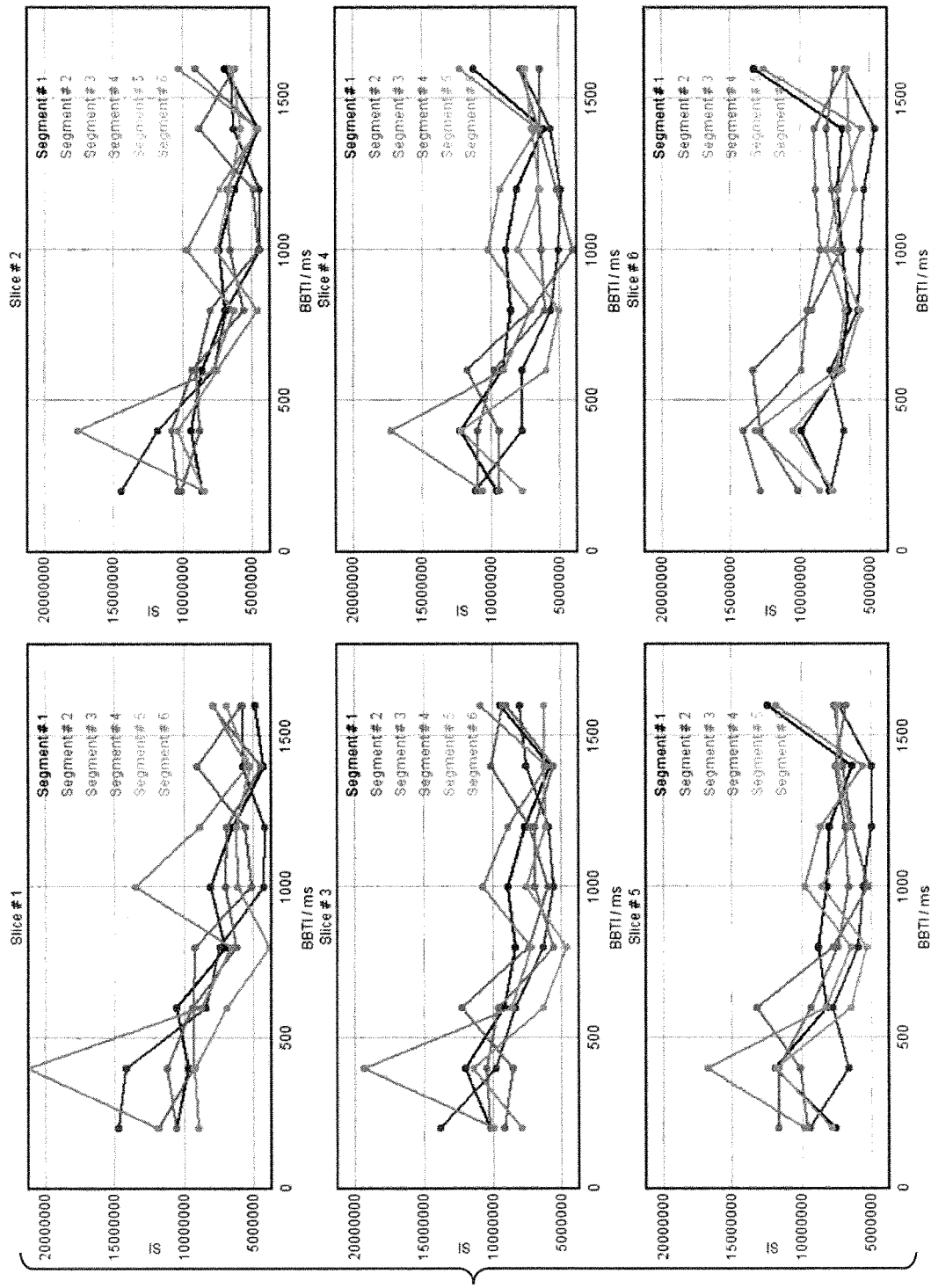
FIGS. 9A-C depict simultaneous one-panel display visualizations of perfusion curves for each segment in each of different slices as a function of BBTI parameter values using different exemplary visualization presentations.
Figure 9B:
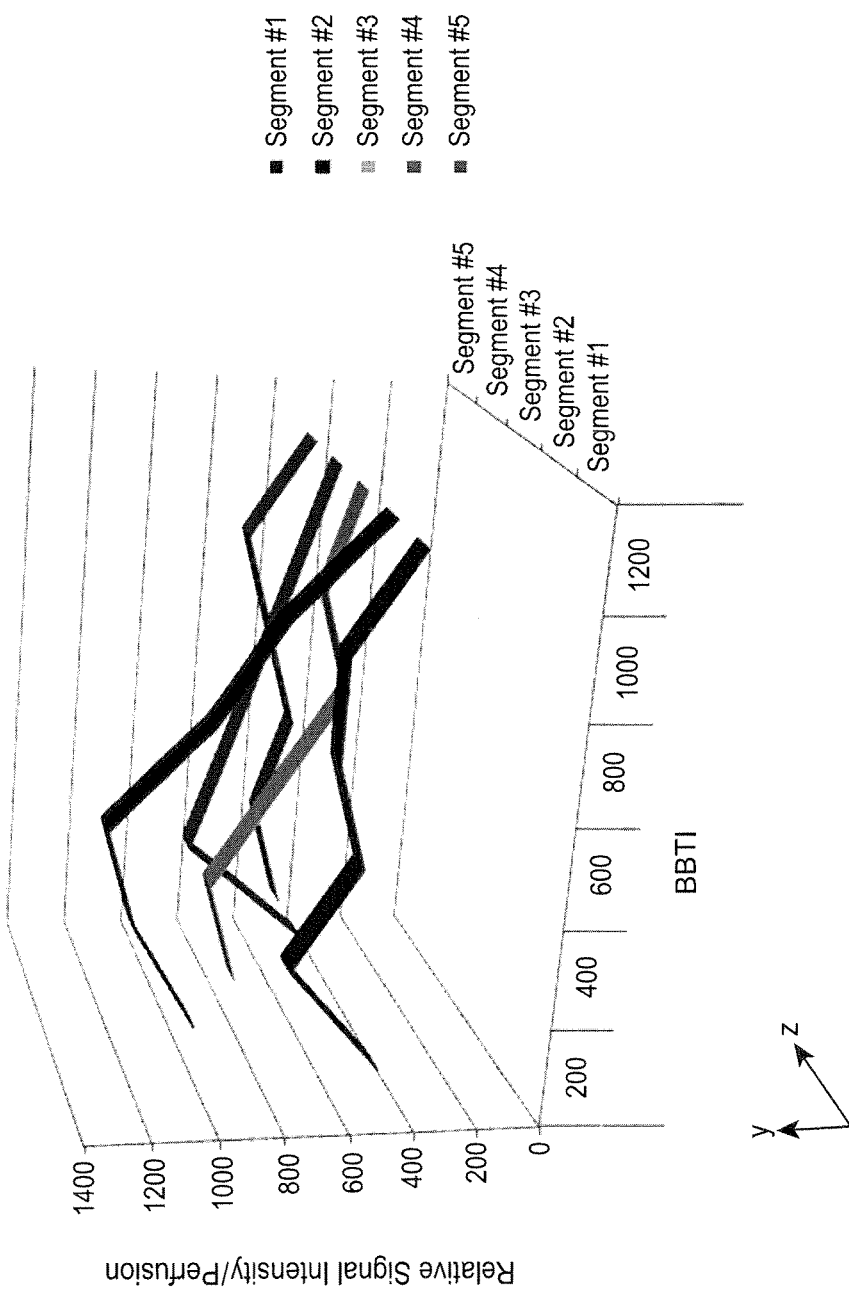
Figure 9C:
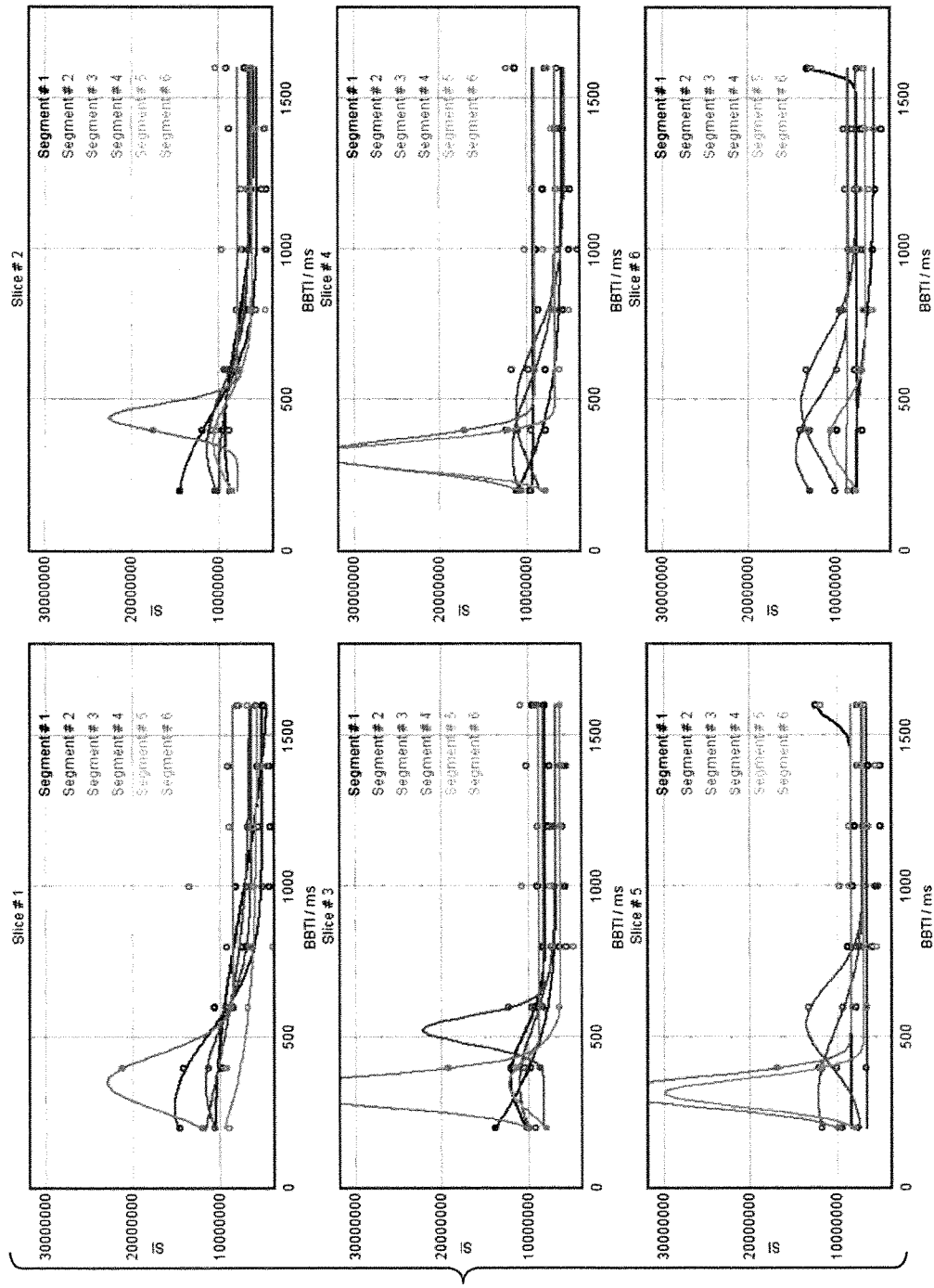

Perfusion curves of each segment in each different slice along the different BBTI images can be created as shown in FIGS. 9A-C. With the saved ROIs of all segments, the perfusion curves can be automatically generated for all segments in all slices. The FIG. 9A example shows unsmoothed raw perfusion curves from one patient. The perfusion curves can be also generated from any ROI that the user has specified.

Conventional polynomial curve fitting or curve smoothing techniques may be applied to assist in further quantification analysis as shown in FIG. 9C. Preferably, two curve fitting equations are used to best fit the perfusion curves. The fitted parameters should be able to describe the perfusion peak intensity, timing of the peak, and the area under the peak. Preferably any identifiable abnormal parameters (e.g., as ascertained by quantitative analysis of the curve fitted perfusion data) should be marked in a fitted parameter table and/or directly on the displayed perfusion curves. Similarly, any region(s) corresponding to the detected abnormalities preferably should be marked directly onto the visualizations of the corresponding AHA segments.

FIG. 9B illustrates a simulated 3D visualization of perfusion curves where (using a typical orientation of orthogonal x,y,z coordinate axes) BBTI values are plotted with respect to an x-axis, relative signal intensity (perfusion) is plotted with respect to a y-axis and slice number is plotted with respect to a z-axis of the visualization display.

Although the perfusion curves are shown in one panel in FIGS. 9A-C, any one perfusion curve can be fetched for overlaid display in FIG. 7A or FIG. 7B when a particular respectively corresponding slice or segment is selected by a user (e.g., by "clicking" a mouse arrow when positioned over that slice or segment of a particular slice at a particular BBTI).

Figure 10A:
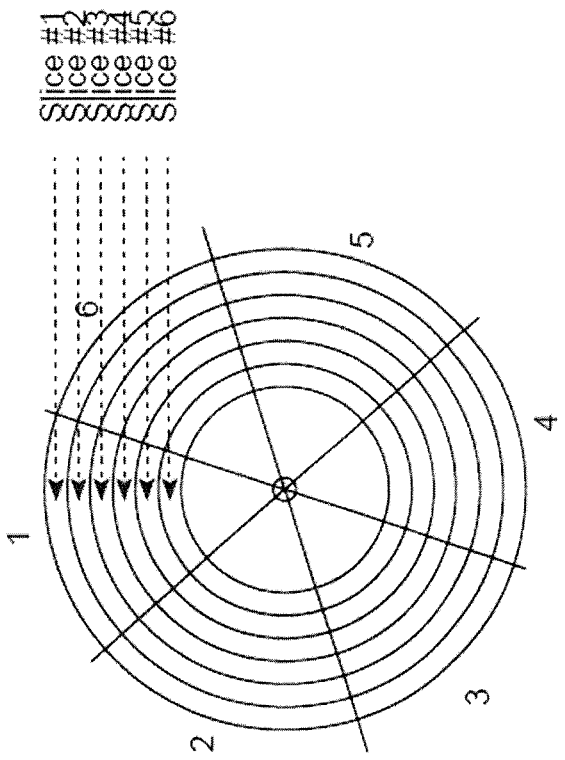
FIGS. 10A-B illustrate new types of bull's eye depictions for better visualization and understanding of relationships between BBTI, signal intensity (SI) which is related to perfusion and/or LV slice numbers constituting substantially contiguous slices within a 3D image of the LV.
Figure 10B:
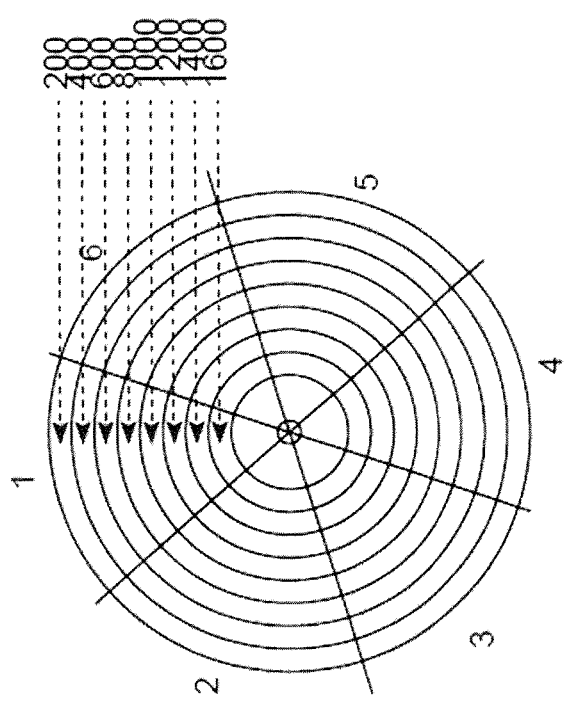

FIGS. 10A-B illustrate new perfusion visualizations using a variation of the well known bull's eye technique. Here, in FIG. 10A, for a given slice number, concentric circles illustrate AHA segments with BBTI values being illustrated along the radial direction. Each bull's eye segment preferably is color-coded for average signal intensity (SI) or relative perfusion value. In this visualization, a trend of SI as a function of BBTI for each cardiac segment can be easily seen and understood. In FIG. 10B, for a given BBTI value, the concentric circles also illustrate AHA segments but now slice numbers are illustrated along the radial direction. Here each bull's eye segment preferably is also color-coded to represent the average SI or perfusion value—and now in this visualization, a trend of SI as a function of slice number at a given BBTI can be easily seen and understood.

The exemplary analysis methods are especially designed for use with our non-contrast dynamic myocardial perfusion techniques. The whole analysis procedure helps visualize perfusion of blood inside myocardium, and to distinguish infarcted regions or ischemic regions from healthy myocardium. The generated perfusion curves are important for quantified evaluation of ischemic disease or infarction.

Figure 11:
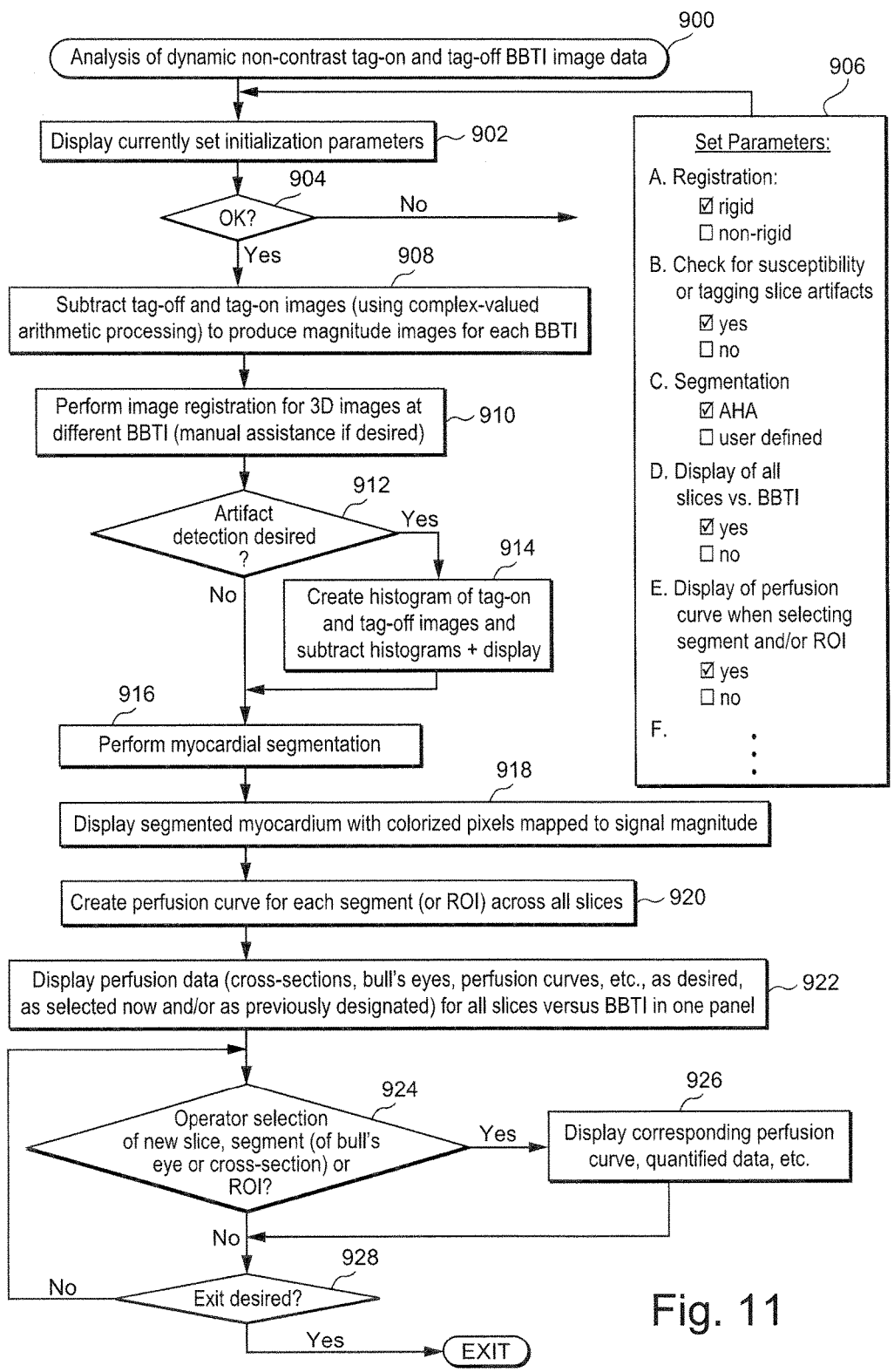
FIG. 11 is a schematic illustration of exemplary computer program code structure for use in the system of FIG. 1 (or a separate image data processing system) in the form of a flow chart for implementing exemplary embodiments of a system for analyzing BBTI tag-on and tag-off images acquired by magnetic resonance imaging (MRI).

FIG. 11 depicts entry into an analysis of dynamic non-contrast tag-on and tag-off BBTI image data at 900. As those in the art will appreciate, this flow chart represents executable computer program code structures such as found in a computer program subroutine that can be called by a higher level application program or operating system.

If desired, the current (initially or last used) set initialization parameters may be displayed at 902 and, if the user is not satisfied with those (as tested at 904), then a parameter initialization screen 906 can be displayed for further operator adjustments/inputs and those will then be displayed again at 902 for acceptance or not at 904.

Once the initialization of the subroutine is found acceptable (if indeed the operator is even given an opportunity for such adjustments), then at 908, previously acquired tag-on and tag-off images are subtracted using complex-valued arithmetic data processing to produce magnitude images for each BBTI value and for each slice of a 3D image.

Subsequently, image registration may be performed at 910 for 3D images at different BBTI values. If desired, manual assistance may be permitted to effect image registration. Of course, image registration may not be required.

If artifact detection is desired as tested at 912, then histograms of tag-on and tag-off images are created at 914 and subtracted so as to provide data representing susceptibility errors and/or errors caused by a tagging pulse affecting the myocardium during image data acquisition. As those in the art will appreciate, block 914 can include tests to detect whether error above a certain threshold is present and, if so, to take remedial action and/or request operator assistance or perhaps even to terminate the process.

At block 916, myocardial segmentation may be performed, if desired. The segmented myocardium is then displayed with colorized pixels mapped to signal magnitude at 918. Perfusion curves are created for each segment (or ROI) for each slice of the 3D image at 920. The slices and/or perfusion curves may be displayed v. BBTI values at 922. As previously discussed, the colorized slice images for the 3D image are preferably displayed in one panel as a function of BBTI values. Similarly, the perfusion curves for each segment and slice of the 3D image are preferably displayed in a single panel.

If the slices are depicted in a single panel, then at 924, an operator is given an opportunity to select a particular segment or ROI at the display (e.g., with a mouse or by touch or the like). If such an operator selection is made, then the corresponding perfusion curve for that particular segment is displayed at 926. The operator is given an option for exit at 928. If and when that desire is indicated, then this subroutine is exited at 930 and control is passed back to the calling higher level program or operating system.

Displaying multi-slice images of any type (i.e., not just perfusion-related images but also non-contrast MR images such as from magnetic resonance angiography (MRA) along a BBTI axis is believed to be new and advantageous. For example, a computerized system for analyzing images acquired by magnetic resonance (MR) imaging may include at least one computer processor coupled to associated memory, display and input/output ports and be configured to: (a) acquire multi-slice non-contrast MR images of left ventricle (LV) myocardium for each of plural BBTI intervals in a region of interest (ROI); and (b) display apical to basal LV slice images as a function of BBTI for plural slices of a 3D image and for plural BBTI values in a single display panel. Such visualization of MR slices as a function of BBTI in a single display panel (e.g., similar to visualizations shown in FIGS. 7A, 7B, 9A-C and/or 10A-B will help users to more quickly "see" important relationships between a succession of BBTI values and various types of MR images acquired with varying BBTI values.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A computerized system for displaying images acquired by magnetic resonance (MR) imaging, said system comprising:
   at least one computer processor coupled to associated memory, display and input/output ports and configured to:
   (a) acquire separate 3D multi-slice non-contrast reconstructed MR images of blood perfusion within left ventricle (LV) myocardium for each of plural inversion time (TI) intervals during a same cardiac phase;
   (b) perform segmentation of each of the 3D multi-slice non-contrast reconstructed MR images; and
   (c) display, to an operator of said system, separate LV slice reconstructed images of blood perfusion at each of plural slice positions from each of the 3D multi-slice non-contrast reconstructed MR images on which the segmentation has been performed, for each of said plural TI time intervals, in sequences of respectively corresponding LV slice reconstructed images of blood perfusion at each of said plural slice positions, as a function of the TI time intervals, simultaneously in a single display panel, in a color map format for each segment resulting from the segmentation.

2. A computerized system for analyzing inversion time (TI) tag-on and tag-off non-contrast images acquired by magnetic resonance imaging (MM) during a same cardiac phase, said system comprising:
   at least one computer processor coupled to associated memory, display and input/output ports and configured to:
   (a) subtract tag-off and tag-on images, each of the tag-off images and each of the tag-on images having been acquired during a same cardiac phase in relation to respective electrocardiogram (ECG) signals and using multi-slice non-contrast imaging, on a pixel-by-pixel basis using both real and imaginary parts of complex-valued acquired MM signals for each of plural TI time intervals to produce difference magnitude 3D images for a 3D volume as a function of the TI time intervals, said difference magnitude 3D images representing blood perfusion in left ventricle (LV) myocardium tissue with blood perfusion data values which are different for normal and abnormal myocardial tissues; and
   (b) display separate LV slice reconstructed MR images of said difference magnitude 3D images for each of plural different slices of said 3D volume at plural of the TI time intervals simultaneously in a single display panel.

3. The system of claim 2, wherein said at least one computer processor is further configured to effect 3D image registration between said difference magnitude 3D images by separately registering, using both said tag-on and said tag-off images, (a) tag-on and/or tag-off images having positive contrast blood where myocardial MR signal intensity is greater than that of left ventricle chamber blood and (b) tag-on and/or tag-off images having negative contrast blood where myocardial MR signal intensity is less than that of left ventricle chamber blood, and
   recording corresponding registration pixel shifts in the difference magnitude 3D images required for the separate registrations.

4. The system of claim 2, wherein said at least one computer processor is further configured to
   perform rigid or non-rigid 3D image registration by separately registering (a) first images, from said tag-off and tag-on images, that have positive contrast blood where myocardial MR signal intensity is greater than that of left ventricle chamber blood and (b) second images, from said tag-off and tag-on images, that have negative contrast blood where myocardial MR signal intensity is less than that of left ventricle chamber blood, and
   recording corresponding registration pixel shifts in the difference magnitude 3D images required for the separate registrations.

5. The system of claim 4, wherein said at least one computer processor is further configured to accept manual user alignment inputs to effect said 3D image registration.

6. The system of claim 2, wherein said at least one computer processor is further configured to
   effect segmentation of said difference magnitude 3D images depicting blood perfusion in imaged LV myocardial tissue, wherein said LV slice reconstructed MR images that are displayed as a function of TI time intervals simultaneously in the single display panel and are selected from: (i) LV slice reconstructed MR images prior to said segmentation; and (ii) LV slice reconstructed MR images after said segmentation.

7. The system of claim 2 wherein said at least one computer processor is configured to segment slices of said difference magnitude 3D images depicting blood perfusion data values in the LV myocardium and to display said blood perfusion data values of the difference magnitude 3D images in at least one bull's eye configuration showing at least one of:
   (a) a segmented slice of LV myocardium having blood perfusion data values plotted along concentric circles for each of the TI time intervals plotted along a radial direction; and
   (b) for one of the TI time intervals, LV myocardium blood perfusion data values plotted along concentric circles for each of different slices of the LV myocardium plotted along a radial direction.

8. The system of claim 2, wherein said at least one computer processor is further configured (A) to generate histograms of said tag-on and tag-off images used to create said difference magnitude 3D images and (B) to subtract said histograms of said tag-on and tag-off images from one another with the subtraction results providing data representing susceptibility error and/or error caused by a tagging pulse affecting the tag-on and tag-off images during image data acquisition processes.

9. The system of claim 2, wherein said at least one computer processor is further configured to (A) perform coronary artery territory segmentation of said difference magnitude 3D images to produce segmented image portions of the left ventricle myocardium blood perfusion data by using a groove between left and right ventricle myocardium as a start point for segmentation and then automatically segmenting said left ventricle myocardium spatially away from said start point, (B) generate an average image blood perfusion data value for each said segmented portion of the left ventricle myocardium, and (C) display said segmented portions of left ventricle myocardium blood perfusion data with visual differences representing their respectively associated different average image blood perfusion data values.

10. The system of claim 2, wherein said at least one computer processor is further configured to
(A) generate from said difference magnitude 3D images at least one curve as a function of the TI time intervals for each of said plural slices, and
(B) display the resulting plural curves in the single display panel, said plural curves being depicted as at least one of: (i) an array of blood perfusion data as a function of the TI time intervals before curve fitting, (ii) an array of curves fitted to blood perfusion data as a function of the TI time intervals, and (iii) quantified curve data obtained from curves fitted to blood perfusion data as a function of the TI time intervals.

11. The system of claim 2, wherein said at least one computer processor is further configured to segment portions of a region of interest (ROI) for each of the plural different slices, and to generate a curve as a function of the TI time interval for each of the plural segmented portions for each of said plural different slices and to display, in the single panel while the separate LV slice reconstructed MR images are displayed, one of said curves corresponding to an operator selected segment of one or more of said plural different slices.

12. A computerized method for analyzing inversion time (TI) tag-on and tag-off non-contrast images acquired by magnetic resonance imaging (MM) during a same cardiac phase, said method comprising:
(a) subtracting, using at least one computer processor coupled to associated memory, display and input/output ports, tag-off and tag-on images, each of the tag-off images and each of the tag-on images having been acquired during a same cardiac phase in relation to respective electrocardiogram (ECG) signals and using 3D multi-slice non-contrast imaging, on a pixel-by-pixel basis using both real and imaginary parts of complex-valued acquired MRI signals for each of plural TI time intervals to produce difference magnitude 3D images of a 3D volume as a function of the TI time intervals, said difference magnitude 3D images representing blood perfusion in left ventricle (LV) myocardium tissue with data values which are different for normal and abnormal myocardial tissues;
(b) performing segmentation, using the at least one computer processor, of each of the difference magnitude 3D images producing respective segmented difference magnitude 3D image corresponding to each said difference magnitude 3D image; and
(c) displaying separate LV slice reconstructed MR images of plural different slices in each of said segmented difference magnitude 3D images at plural of the TI time interval values simultaneously in a single display panel, in a color map format for each segment resulting from the segmentation.

13. The method of claim 12 further comprising, effecting, using said at least one computer processor, 3D image registration between said difference magnitude 3D images by separately registering, using both said tag-on and said tag-off images, (a) tag-on and/or tag-off images having positive contrast blood where myocardial MR signal intensity is greater than that of left ventricle chamber blood, and (b) tag-on and/or tag-off images having negative contrast blood where myocardial MR signal intensity is less than that of left ventricle chamber blood, and
recording, using the at least one computer processor, corresponding registration pixel shifts in the difference magnitude 3D images required for the separate registrations.

14. The method of claim 12 further comprising, performing, using the at least one computer processor, rigid or non-rigid 3D image registration by separately registering (a) first images, from said tag-off and tag-on images, that have positive contrast blood where myocardial MR signal intensity is greater than that of left ventricle chamber blood and (b) second images, from said tag-off and tag-on images, that have negative contrast blood where myocardial MR signal intensity is less than that of left ventricle chamber blood, and
recording, using the at least one computer processor, registration pixel shifts required for the separate registrations.

15. The method of claim 14 further comprising, accepting, using the at least one computer processor, manual user alignment inputs to effect said 3D image registration.

16. The method of claim 12, wherein said performing segmentation includes using a groove between left and right ventricle myocardium as a start point, and then automatically segmenting said left ventricle myocardium starting from said start point, wherein said LV slice images that are displayed as a function of BBTI time intervals in the single display panel are selected from: (i) LV slice images of blood perfusion data prior to said segmentation; and (ii) LV slice images of blood perfusion data after said segmentation.

17. The method of claim 12 further comprising, using the at least one computer processor, (A) generating histograms of said tag-on and tag-off images used to create said difference magnitude 3D images and (B) subtracting said histograms of said tag-on and tag-off images from one another with the subtraction results providing data representing susceptibility error and/or error caused by a tagging pulse affecting the tag-on and/or tag-off myocardium images during image data acquisition processes.

18. The method of claim 12, wherein said performing segmentation includes producing said segments by marking a groove between left and right ventricle myocardium as a start point for segmentation and then automatically segmenting said left ventricle myocardium spatially away from said start point, and wherein the method further comprises, using the at least one computer processor, (A) generating an average image blood perfusion data value for each said segment, and (B) displaying said segments with visual differences representing their respectively associated different average image blood perfusion data values.

19. The method of claim 12 further comprising, using the at least one computer processor, (A) generating from said difference magnitude 3D images at least one curve as a function of the TI time intervals for each of said plural slices, and
(B) displaying the resulting plural curves in the single display panel, said plural curves depicting at least one of: (i) an array of blood perfusion data as a function of the TI time intervals before curve fitting, (ii) an array of curves fitted to blood perfusion data as a function of the TI time intervals, and (iii) quantified curve data obtained from curves fitted to blood perfusion data as a function of the TI time intervals.

20. The method of claim 12 wherein the performing segmentation includes producing said segments by segmenting a region of interest (ROI) for said each of plural different slices of one of said difference magnitude 3D images, and wherein the method further comprises generating a curve as a function of the TI time intervals for each of the segments of the ROI for each of plural slices of one of said difference magnitude 3D images and displaying one of said curves corresponding to an operator selected segment of one of the displayed slices.

21. The method of claim 12, wherein the method further comprises displaying said data values of the difference magnitude 3D images in at least one bull's eye configuration showing at least one of:
(a) a segmented slice of said LV myocardium blood perfusion data values plotted along concentric circles for each of different the TI time intervals plotted along a radial direction; and
(b) for one of the TI time intervals, LV myocardium blood perfusion data values plotted along concentric circles for each of different slices of the LV myocardium plotted along a radial direction.

22. A magnetic resonance imaging (MM) system comprising:
an MRI gantry having static and gradient magnet assemblies and at least one radio frequency (RF) coil;
MRI control circuits connected to control components within said MRI gantry and configured to effect MRI data acquisition sequences of RF and gradient magnetic pulses which elicit MM signals, to acquire and process said elicited MM signals into MR image data in conjunction (a) with use of an initial spatially-selective nuclear magnetic resonance (NMR) RF tag pulse (tag-on) in a data acquisition sub-sequence and (b) without use of an initial spatially-selective NMR RF tag pulse (tag-off) in a data acquisition sub sequence;
said MM control circuits being configured to
(A) acquire multi-dimensional MR k-space data from the elicited MRI signals using said tag-on and tag-off data acquisition sub-sequences for each of plural time to inversion (TI) time intervals during a same cardiac phase without using an injected contrast agent;
(B) reconstruct said acquired k-space data into spatial domain tag-on and tag-off MR image data, each of the tag-off MR image data and each of the tag-on MR image data having been acquired during a same cardiac phase in relation to respective electrocardiogram (ECG) signals and using 3D multi-slice imaging;
(C) subtract said reconstructed tag-off and tag-on MR image data for each of plural TI time intervals using both real and imaginary parts of complex-valued acquired MRI signals from the elicited MM signals to produce difference magnitude 3D image data as a function of time having a corresponding blood flow time and/or relative peak blood flow magnitude, or lack thereof, which differentiates between normal, ischemic and infarct tissues;
(D) perform segmentation of each of the difference magnitude 3D image data; and
(E) concurrently display plural separate left ventricle (LV) slice reconstructed MR images of said difference magnitude 3D image data on which the segmentation has been performed, for each of plural slices of a 3D volume as visually different display data values (a) for normal, ischemic and infarct tissues based on said difference magnitude 3D image data and (b) at the plural TI time intervals simultaneously in a single display panel, in a color map format for each segment resulting from the segmentation.

23. The MRI system of claim 22, wherein said MRI control circuits are further configured (A) to generate histograms of said tag-on and tag-off MR image data used to create said difference magnitude 3D image data and (B) to subtract said histograms of said tag-on and tag-off images from one another with the subtraction results providing data representing susceptibility error and/or error caused by an RF tag pulse affecting the tag-on and tag-off images during image data acquisition processes.

24. The MRI system of claim 22, wherein said performing segmentation includes performing coronary artery territory segmentation of said difference magnitude 3D image data to produce said segments of the left ventricle myocardium by using a groove between left ventricle myocardium and right ventricle myocardium as a start point for segmentation and then automatically segmenting said left ventricle myocardium spatially away from said start point,
and wherein said MM control circuits are further configured to generate an average image data value for each said segmented portion of the left ventricle myocardium, and display said segments of left ventricle myocardium with visual differences representing their respectively associated different average image data values.

25. The MRI system of claim 22, wherein said MRI control circuits are further configured to generate at least one curve as a function of the TI time intervals for each of said plural slices and to display the resulting plural curves in the single display panel.

26. The MRI system of claim 22, wherein said performing segmentation includes producing said segments by segmenting a region of interest (ROI) for each of said plural slices,
and wherein said MRI control circuits are further configured to generate a curve as a function of the TI time intervals for each of the segments of the ROI for each of plural slices of said difference magnitude 3D image data and to also display one of said curves corresponding to an operator selected segment of one of the plural slices in said single display panel.

* * * * *